United States Patent

Hasegawa et al.

[11] Patent Number: 5,808,144
[45] Date of Patent: Sep. 15, 1998

[54] BENZENE DERIVATIVES

[75] Inventors: Masaichi Hasegawa; Takumi Takeyasu; Naoki Tsuchiya; Naoki Hase; Katsushi Takahashi; Takashi Kamimura, all of Hino, Japan

[73] Assignee: Teijin Limited, Osaka, Japan

[21] Appl. No.: 875,284

[22] PCT Filed: Nov. 27, 1995

[86] PCT No.: PCT/JP96/03456

§ 371 Date: Jul. 23, 1997

§ 102(e) Date: Jul. 23, 1997

[87] PCT Pub. No.: WO97/19910

PCT Pub. Date: May 6, 1997

[30] Foreign Application Priority Data

Nov. 27, 1995 [JP] Japan .................................. 7-307222
Aug. 29, 1996 [JP] Japan .................................. 8-228367

[51] Int. Cl.[6] .......................... C07C 229/00; C07C 321/00
[52] U.S. Cl. .................. 562/455; 560/18; 560/45
[58] Field of Search .................. 560/18, 45; 562/455

[56] References Cited

PUBLICATIONS

Database CAPLUS, No. 120:134055, Oe et al., 'Preparation of arylalkananilides as ACAT inhibitors (WO9315043),' abstract, Aug. 5, 1993.

Primary Examiner—Gary Geist
Assistant Examiner—Brian J. Davis
Attorney, Agent, or Firm—Foley & Lardner

[57] ABSTRACT

Novel benzene derivatives of the formula (I) shown below, pharmacological salts thereof, pharmacological solvates of the above-mentioned benzene derivatives and salts, pharmaceutical compositions including, as active ingredients, the above-mentioned compounds, and especially, prophylactic or therapeutic medicines for allergic diseases.

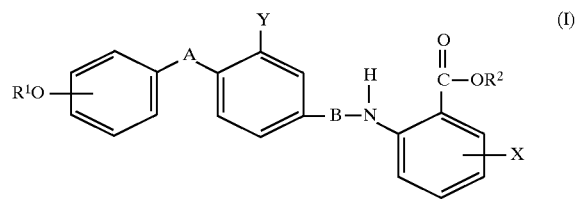

wherein $R^1$=H, $C_1$–$C_{12}$ cyclic or straight or branched chain alkyl group (which may be substituted by one or more $C_6$–$C_{10}$ aryloxy groups), $C_7$–$C_{12}$ aralkyl group (of which the aryl group may be substituted one or more of halogen, methyl and methoxy, or $C_3$–$C_{10}$ alkenyl which may be substituted by one or more phenyl groups; A=O, S or $CH_2$ group, B=CO or $CZ_2$CO group (Z=H or F), $R^2$=H or $C_1$–$C_4$ alkyl group, X=halogen or methyl group, and Y=H, $NO_2$ or CN group.

15 Claims, No Drawings

BENZENE DERIVATIVES

DESCRIPTION

1. Technical Field

The present invention relates to new benzene derivatives, pharmacologically acceptable salts thereof or pharmacologically acceptable solvates of the above-mentioned benzene derivatives and salts thereof, pharmaceutical compositions comprising same as active ingredients, and pharmaceutical applications of the compositions. More particularly, the present invention relates to new benzene derivatives in which three benzene moieties are bonded through specific bonding groups, pharmacologically acceptable salts thereof or pharmacologically acceptable solvates of the above-mentioned benzene derivatives and salts thereof, pharmaceutical compositions comprising same as an active ingredient, and pharmaceutical applications of the compositions. The new benzene derivatives, salts thereof and solvates of the benzene derivatives and salts thereof exhibit excellent inhibitory activity against production of IgE antibodies and are useful as prophylactic or therapeutic medicines for allergic diseases.

2. Background Art

In various allergic diseases represented by asthma and atopic dermatitis, it is known that various chemical mediators represented by leucotriene and thromboxane perform a large role in the allergic reactions. The allergic reactions are derived from binding (sensitization) of a Fc region of the immunoglobulin E (IgE) antibodies with receptors of cell membranes. When an allergen penetrates into the body in the sensitized conditions, the chemical mediators are released by bonding the allergen with the IgE antibodies on the cell membranes, and thus the allergic diseases occur. In fact, it is known that the concentration of the IgE antibodies in the serum or tissue of the patients with the allergic diseases is higher than that of normal persons. Further, it is known that in the patients with the allergic diseases, a messenger RNA of interleukin 4 (IL-4) is produced in lymphocytes, and the messenger RNA performs an important role on the production of the IgE antibodies. The sthenia in the production of the IgE antibodies through the IL-4 is considered to greatly influence deterioration of pathosis of the diseases. Accordingly, if the production of the IgE antibodies could be inhibited, it is possible that the prophylaxis and/or therapy of the allergic diseases can be greatly promoted. However, as a therapeutic medicine for the allergic diseases, histamine antagonists, which belong to the chemical mediators and release-inhibiters (sodium chromoglycate) of the chemical mediators from the cells, are mainly used, and medicines for preventing or treating the allergic diseases by inhibiting the production of the IgE antibodies have not yet been subjected to practical use. Namely, if a new inhibitor for the production of the IgE antibodies could be obtained, it could block a step before the release of the chemical mediators, and the allergic diseases could be prevented and/or treated in an etiotropic way.

Japanese Unexamined Patent Publication No. 1-287,066 discloses that certain compounds having both a naphthalene moiety and an anthranilic acid moiety, for example, N-(2-naphthoyl)anthranilic acid have an anti-allergic activity or 5-lipoxygenase-inhibiting activity. The compounds described in the above-mentioned publication are, however, -characterized by having the naphthalene structure. Also, the above-mentioned publication does not disclose or suggest whether or not the compounds have the IgE antibody production-inhibiting activity.

Also, Japanese Unexamined Patent Publication No. 63-270634 discloses that certain compounds having both a naphthalene moiety and an anthranilic acid moiety have a 5-lipoxygenase-inhibiting activity and anti SRS-A activity. The compounds described in the above-mentioned publication are, however, characterized in that, in the compounds, the naphthalene moiety and the anthranilic acid moiety are bonded with each other through an alkyl chain. Also, the above-mentioned publication includes no statement concerning the IgE antibody production-inhibiting performance of the compounds.

Further, Japanese Unexamined Patent Publication No. 1-106,818, International Application Publication WO 90/12001 specification and Japanese Unexamined Patent Publication No. 7-285,858 disclose certain compounds having both a naphthalene moiety and an anthranilic acid moiety and exhibiting an anti-allergic activity, and IgE antibody production-inhibiting performance. All the compounds disclosed in the publications are, however, characterized by having, as an indispensable structure, a naphthalene ring or hydronaphthalene ring structure. Especially, the compounds disclosed in Japanese Unexamined Patent Publication No. 1-106,818 have such structural characteristics that a cyclopropane ring structure is contained therein. The group of compounds disclosed in International Application Publication WO 90/12001 specification are characterized in that hydrogen atoms in the naphthalene ring are substituted by two oxygen atoms and a sulfur atom, and thus these compounds are clearly different from the group of the compounds of the present invention. Further, in the group of compounds of Japanese Unexamined Patent Publication No. 7-285,858, the naphthalene ring and the anthranilic acid ring are bonded through a group of carbon atom chains. Therefore, these compounds are definitely different from the group of compounds of the present invention. Also, in Macromolecular Chemistry (Makromol. Chem.), Vol. 130, 103 to 144 (1969), compounds having three benzene rings bonded to each other through a ether bond and an amide bond are shown. These compounds have such a structural feature that a nitro group is located in a terminal thereof, and thus are definitely different from the compounds of the present invention. In addition, the above-mentioned literature is quite silent as to the IgE antibody production-inhibiting performance of these compounds. Further, Japanese Unexamined Patent Publication No. 60-116,657 reports aniline derivatives having a leucotriene antagonistic performance. These aniline derivatives disclosed in the publication are definitely different from the group of compounds of the present invention. All the compounds recited in examples of the publication are cinnamoylanthranilic acid derivatives having a benzene moiety and an anthranilic acid moiety bonded to each other through a double bond.

DISCLOSURE OF THE INVENTION

An object of the present invention is to provide new benzene derivatives, pharmacologically acceptable salts thereof or pharmacologically acceptable solvates of the above-mentioned benzene derivatives and salts thereof, which are useful for medicines, pharmaceutical compositions comprising the above-mentioned benzene derivatives, salts and solvates as a principal ingredient, and prophylactic or therapeutic medicines for allergic diseases comprising the pharmaceutical compositions.

The benzene derivatives in accordance with the present invention are represented by the formula (I)

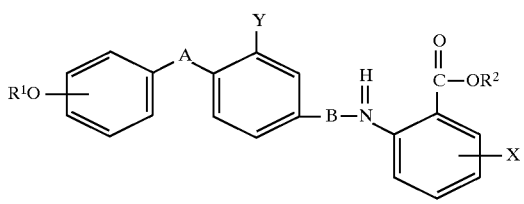

(I)

in which formula (I), $R^1$ represents a hydrogen atom, a $C_1$ to $C_{12}$ cyclic, straight chain or branched chain alkyl group which may be substituted with at least one $C_6$ to $C_{10}$ aryloxy group, a $C_7$ to $C_{12}$ aralkyl group of which the aryl group may be substituted by at least one member selected from halogen atoms, a methyl group and a methoxy group, or a $C_3$ to $C_{10}$ alkenyl group which may be substituted by at least one phenyl group; A represents an —O—, —S— or —$CH_2$— group; B represents an —CO— or —$CZ_2CO$— group in which Z represents a hydrogen atom or a fluorine atom; $R^2$ represents a hydrogen atom, or a $C_1$–$C_4$ lower alkyl group; X represents a hydrogen atom, a halogen atom or a methyl group; and Y represents a hydrogen atom, a nitro group or a nitrile group, and may be in the form of pharmacologically acceptable salts thereof or pharmacologically acceptable solvates of the above-mentioned benzene derivatives and salts thereof.

The pharmaceutical compositions of the present invention are those comprising the benzene derivatives of the formula (I), the pharmacologically acceptable salts thereof or the pharmacologically acceptable solvates of the above-mentioned benzene derivatives and salts thereof, and pharmacologically acceptable carriers.

Also, the prophylactic or therapeutic medicines of the present invention for allergic diseases are characterized by comprising the pharmaceutical compositions as an active ingredient, and having an IgE antibody production-inhibiting performance.

BEST MODE OF CARRYING OUT THE INVENTION

In the formula (I) representing the benzene derivatives of the present invention, $R^1$ represents a hydrogen atom, a $C_1$ to $C_{12}$ cyclic, straight chain or branched chain alkyl group which may be substituted by at least one $C_6$ to $C_{10}$ aryloxy group, a $C_7$ to $C_{12}$ aralkyl group of which the aryl group may be substituted by at least one member of halogen atoms and methyl and methoxy groups, or a $C_3$ to $C_{10}$ alkenyl group which may be substituted by at least one phenyl group.

In the formula (I), $R^1$ represents a $C_1$ to $C_{12}$ cyclic, straight chain or branched chain alkyl group. The alkyl group can be selected from, for example, methyl, ethyl, propyl, 2-propyl, 1- or 2-methylpropyl, 2,2-dimethylpropyl, n- or tert-butyl, 2-ethylbutyl, 2- or 3-methylbutyl, pentyl, hexyl, heptyl, octyl, decyl, dodecyl, cyclopropyl, cyclopropylmethyl, cyclobutyl, cyclopentyl, cyclohexyl, cyclophexylmethyl, cyclooctyl, cycloheptyl, cyclododecyl, 2-phenoxyethyl, 2-phenoxypropyl and 4-phenoxybutyl groups.

$R^1$ also represents a $C_7$ to $C_{12}$ aralkyl group. The halogen atoms, by which the aryl group in the aralkyl group may be substituted, include fluorine, chlorine and bromine atoms.

The aralkyl group represented by $R^1$ is selected from, for example, benzyl, 2-, 3- and 4-chlorobenzyl, 2-, 3- and 4-methoxybenzyl, 2-, 3- and 4-methylbenzyl, α- or β-phenylethyl, 3-phenylpropyl, 2-phenyl-2-propyl, 2-phenyl-1-cyclohexyl, (1-phenylcyclopropyl)methyl, (1-phenylcyclopentyl)methyl, and 1-, and 2-naphthylmethyl groups.

$R^1$ also may represent a $C_3$ to $C_{10}$ alkenyl group. The alkenyl group is selected from, for example, allyl, methallyl, crotyl, 3-butenyl, 4-pentenyl, 5-hexenyl, 7-octenyl, geranyl, cinnamyl, 2-cyclohexenyl, (3-cyclohexenyl)methyl and 1,4-pentadien-3-yl.

Also, $R^1$ may represent a hydrogen atom.

Among the atoms and groups represented by $R^1$, preferred ones are a hydrogen atom and ethyl, ethyl, propyl, 2-propyl, 1- or 2-methylpropyl, 2,2-dimethylpropyl, n- or tert-butyl, 2-ethylbutyl, (2- or 3-methylbutyl, pentyl, hexyl, heptyl, octyl, decyl, dodecyl, cyclopropylmethyl, cyclopentyl, cyclohexyl, cyclohexylmethyl, cyclooctyl, cycloheptyl, cyclododecyl, 2-phenoxyethyl, 3-phenoxypropyl, benzyl, 4-chlorobenzyl, 4-methylbenzyl, 4-methoxybenzyl, α- or β-phenylethyl, 3-phenylpropyl, 1- or 2-naphthylmethyl, allyl, 3-butenyl, 4-pentenyl, 5-hexenyl and 7-octenyl.

Among them, $R^1$ preferably represents a hydrogen atom, a $C_1$ to $C_{12}$ chain or cyclic saturated hydrocarbon group, or a $C_7$ to $C_{12}$ aralkyl group, more preferably a $C_5$ to $C_{12}$ cyclic saturated hydrocarbon group, for example, a cyclohexyl, cycloheptyl, cyclooctyl, cyclopentyl or cyclododecanyl group, or a $C_3$ to $C_8$ branched chain saturated hydrocarbon group, still more preferably, a branched chain alkyl group in which the branching occurs at a location adjacent to an oxygen atom, for example, isopropyl or 3-pentyl group, and a benzyl group.

In the formula (I), A represents an —O—, —S— or —$CH_2$— group. Among them, A preferably represents an —O—, —S— bond.

In the formula (I), B represents a —CO— or —$CZ_2CO$— group wherein Z represents a hydrogen or fluorine atom. Among them, B repreferably represents a —$CH_2CO$— group.

In the formula (I), $R^2$ represents a hydrogen atom or a $C_1$ to $C_4$ lower alkyl group. The lower alkyl group represented by $R^2$ includes methyl, ethyl, n- and iso-propyl, n-, iso- and tert-butyl groups. Preferably $R^2$ is a hydrogen atom, a methyl group or an ethyl group. More preferably $R^2$ is a hydrogen atom.

In the formula (I), X represents a hydrogen atom, a halogen atom or a methyl group. Among them, X is preferably a hydrogen atom, a fluorine atom, or a chlorine atom.

Further in the formula (I), Y represents a hydrogen atom, a nitro group or a nitrile group. Among them, Y is preferably a hydrogen atom or a nitro group.

In the benzene derivatives of the present invention represented by the formula (I), preferably, $R^1$ is a hydrogen atom, a $C_1$ to $C_{12}$ alkyl group or a $C_7$ to $C_{17}$ aralkyl group, A is an —O— bond and B is a —CO— group or —$CH_2CO$— group. These compounds are advantageous in a high IgE antibody production-inhibiting activity thereof in vitro.

In the benzene derivatives of the present invention represented by the formula (I), $R^1$ may be a hydrogen atom, a $C_5$ to $C_{12}$ cyclic alkyl group, a $C_3$ to $C_8$ branched chain alkyl group or a benzyl group, A is an —O— bond, B is —$CH_2CO$— group, and $R^2$ represents a hydrogen atom. These compounds are advantageous in a further enhanced IgE antibody production-inhibiting activity thereof in vitro.

In the benzene derivatives of the present invention represented by the formula (I), $R^1$ may be a $C_5$ to $C_{12}$ cyclic alkyl group, the groups of the following formula:

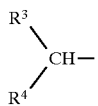

wherein $R^3$ and $R^4$ respectively and independently from each other represent a methyl, ethyl or n-propyl group, or a benzyl group. Such compounds are advantageous in a high IgE antibody production-inhibiting activity thereof in vitro and in vivo.

In the formula (I), when X represents a halogen atom or a methyl group, the substituent X is preferably located in a 4- or 5-position of the benzene ring to which the substituent X is attached, with respect to the —$COOR^2$ group. The group X located in the 4- or 5-position causes an advantage in that the group X inhibits an inactivation of the compounds of the formula (I) due to metabolism and causes the pharmaceutical effect of the compounds to be kept long.

In the formula (I), the substituent represented by $R^1O$ is preferably located in a 4-position of the benzene ring to which the $R^1O$ is attached, with respect to the A group. The substituent $R^1O$ located in the 4-position is advantageous in that the resultant IgE antibody production-inhibiting activity in vitro is higher than that derived from the substitutuent $R^1O$ located in a 2-or 3-position.

In the formula (I), when $R^2$ represents a hydrogen atom, namely the group represented by —$COOR^2$ is a —COOH group, the carboxylic group may be converted to a pharmacologically acceptable non-toxic salt thereof, if necessary. The cations for forming the non-toxic carboxylic salts include alkali metal ions, for example, $Na^+$ and $K^+$ ions; alkaline earth metal ions, for example, $Mg^{2+}$ and $Ca^{2+}$ ions, other non-toxic equivalent metal ions, for example, $Al^{3+}$ and $Zn^{2+}$ ions; ammonia; and organic bases, for example, triethylamine, ethylenediamine, propanediamine, pyrrolidine, piperidine, piperadine, pyridine, lysine, choline, ethanolamine, N,N-dimethylethanolamine, 4-hydroxypiperidine, glucosamine, and N-methylglucamine. Among these salt-forming cations, $Na^+$, $Ca^{2+}$ ions and organic bases such as lisine, choline, N,N-dimethylethanolamine and N-methylglucamine are preferably used.

The benzene derivatives of the formula (I) and non-toxic salts thereof may be converted to pharmacologically acceptable solvates thereof. The solvents for forming the above-mentioned solvates may be selected from water, methyl alcohol, ethyl alcohol, n- and iso-propyl alcohols, n- and tert-butyl alcohols, acetonitrile, acetone, methylethyl ketone, chloroform, ethyl acetate, diethylether, tert-butylmethylether, benzene, toluene, DMF and DMSO. Among these solvents, water, methyl alcohol, ethyl alcohol, n- and iso-propyl alcohols and acetonitrile are preferably employed.

The benzene derivatives represented by the formula (I) of the present invention are expected, in comparison with conventional IgE antibody production-inhibiting agents, to exhibit the following effects.

(1) Since the benzene derivatives have a relatively low molecular weight, they are expected to be absorbed with a high absorption through an intestinal membrane when they are orally dosed.

(2) Since they have a high partition ratio (log P) of 2-octanol to water, they are expected to exhibit a high absorption and a good medicament kinetics in blood.

(3) Since the benzene derivatives can be prepared by coupling reactions of three benzene derivatives, the resultant benzene derivatives are cheap and easily available, and thus the production cost thereof is expected to be low.

The preferable examples of the benzene derivatives of the formula (I) of the present invention include, for example, those as shown below.

| Compound No. | Chemical name |
| --- | --- |
| 1 | Methyl 2-(4-(4-benzyloxyphenylthio) phenylacetamido)benzoate |
| 2 | 2-(4-(4-benzyloxyphenylthio) phenylacetamido)benzoic acid |
| 3 | Methyl 2-(4-(4-benzyloxyphenoxy) phenylacetamido)benzoate |
| 4 | 2-(4-(4-benzyloxyphenoxy) phenylacetamido)benzoic acid |
| 5 | Methyl 2-(4-(4-hydroxyphenoxy) phenylacetamido benzoate |
| 6 | 2-(4-benzyloxyphenoxy)benzamido) benzoic acid |
| 7 | Methyl 2-(4-(4-cyclohexyloxyphenoxy) phenylacetamido)benzoate |
| 8 | 2-(4-(4-cyclohexyloxyphenoxy) phenylacetamido)benzoic acid |
| 9 | 2-(4-(4-cyclohexylmethyloxyphenoxy) phenylacetamido)benzoic acid |
| 10 | 2-(4-(4-cycloheptyloxyphenoxy) phenylacetamido)benzoic acid |
| 11 | Methyl 2-(4-(4-cyclopentyloxyphenoxy) phenylacetamido)benzoate |
| 12 | 2-(4-(4-cyclopentyloxyphenoxy) phenylacetamido)benzoic acid |
| 13 | Methyl 2-(4-(4-cyclooctyloxyphenoxy) phenylacetamido)benzoate |
| 14 | 2-(4-(4-cyclooctyloxyphenoxy) phenylacetamido)benzoic acid |
| 15 | Methyl 2-(4-(4-cyclododecanyloxy-phenoxy)phenylacetamido)benzoate |
| 16 | 2-(4-(4-cyclododecanyloxyphenoxy) phenylacetamido)benzoic acid |
| 17 | Methyl 2-(4-(4-isopropyloxyphenoxy) phenylacetamido)benzoate |
| 18 | 2-(4-(4-isopropyloxyphenoxy) phenylacetamido)benzoic acid |
| 19 | Methyl 2-(4-(4-(3-pentyloxy)phenoxy) phenylacetamido)benzoate |
| 20 | 2-(4-(4-(3-pentyloxy)phenoxy) phenylacetamido)benzoic acid |
| 21 | Methyl 2-(4-(4-cyclooctyloxyphenoxy) benzamido)benzoate |
| 22 | 2-(4-(4-cyclooctyloxyphenoxy) benzamido)benzoic acid |
| 23 | Methyl 2-(4-(4-(2,2-dimethylpropyloxy) phenoxy)phenylacetamido benzoate |
| 24 | 2-(4-(4-(2,2-dimethylpropyloxy) phenoxy)phenylacetamido)benzoic acid |
| 25 | 2-(4-(4-phenylpropyloxphenoxy) benzamido)benzoic acid |
| 26 | 2-(4-(4-(n-octyloxy)phenoxy) benzamido)benzoic acid |
| 27 | 2-(4-(4-allyloxyphenoxy)benzamido) benzoic acid |
| 28 | 2-(4-(4-hydroxyphenoxy)phenyl-acetamido)benzoic acid |
| 29 | Methyl 2-(4-(4-hydroxyphenoxy) benzamido)benzoate |
| 30 | 2-(4-(4-hydroxyphenoxy)benzamido) benzoic acid |
| 31 | Methyl 2-(4-(4-cyclooctyloxyphenoxy)-3-nitrobenzamido)benzoate |
| 32 | 2-(4-(4-cyclooctyloxyphenoxy)-3-nitrobenzamido)benzoic acid |
| 33 | Methyl 2-(4-(3-benzyloxyphenoxy) phenylacetamido)-5-chlorobenzoate |
| 34 | 2-(4-(3-benzyloxyphenoxy)phenyl-acetamido)-5-chlorobenzoic acid |
| 35 | 2-(4-(4-cyclooctyloxyphenoxy) phenylacetamido)-5-chlorobenzoic acid |
| 36 | Methyl 2-(4-(3-benzyloxyphenoxy) |

-continued

| Compound No. | Chemical name |
|---|---|
| | phenylacetamido)-4-fluorobenzoate |
| 37 | 2-(4-(3-benzyloxyphenoxy)phenyl-acetamido)-4-fluorobenzoic acid |
| 38 | Methyl 2-(4-(3-benzyloxyphenoxy)phenylacetamido)-5-methylbenzoate |
| 39 | 2-(4-(3-benzyloxyphenoxy)phenyl-acetamido)-5-methylbenzoic acid |
| 40 | Methyl 2-(4-(4-cyclooctyloxyphenoxy)phenylacetamido)-5-methylbenzoate |
| 41 | 2-(4-(4-cyclooctyloxyphenoxy)phenylacetamido)-5-methylbenzoic acid |
| 42 | Methyl 2-(4-(4-(2-methylpropyloxy)phenoxy)phenylacetamido)benzoate |
| 43 | 2-(4-(4-(2-methylpropyloxy)phenoxy)phenylacetamido)benzoic acid |
| 44 | Methyl 2-(4-(2-benzyloxyphenoxy)phenylacetamido)benzoate |
| 45 | 2-(4-(2-benzyloxyphenoxy)phenylacetamido)benzoic acid |
| 46 | Methyl 2-(4-(2-cyclooctyloxyphenoxy)phenylacetamido)benzoate |
| 47 | 2-(4-(2-cyclooctyloxyphenoxy)phenylacetamido)benzoic acid |
| 48 | Methyl 2-(4-(4-(2-phenoxyethoxy)phenoxy)phenylacetamido)benzoate |
| 49 | 2-(4-(4-(2-phenoxyethoxy)phenoxy)phenylacetamido)benzoic acid |
| 50 | Methyl 2-(4-(4-(3-butenyloxy)phenoxy)phenylacetamido)benzoate |
| 51 | 2-(4-(4-(3-butenyloxy)phenoxy)phenylacetamido)benzoic acid |
| 52 | Methyl 2-(4-(4-(2-ethylbutyloxy)phenoxy)phenylacetamido)benzoate |
| 53 | 2-(4-(4-(2-ethylbutyloxy)phenoxy)phenylacetamido)benzoic acid |
| 54 | Methyl 2-(4-(4-butyloxyphenoxy)phenylacetamido)benzoate |
| 55 | 2-(4-(4-butyloxyphenoxy)phenyl-acetamido)benzoic acid |

The above-mentioned compounds may be in the form of pharmacologically acceptable salts thereof or of pharmacologically acceptable solvates of the above-mentioned compounds and salts thereof.

The benzene derivatives of the formula (I) of the present invention can be produced in accordance with, for example, the scheme as indicated below. Namely, the target compound of the formula (I) can be obtained by condensing a carboxylic acid compound of the formula (II) having two benzene skeletons with an aniline compound of the formula (III).

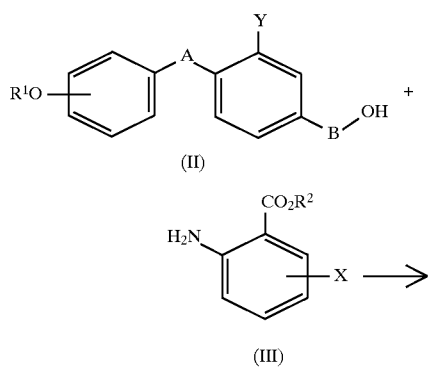

-continued

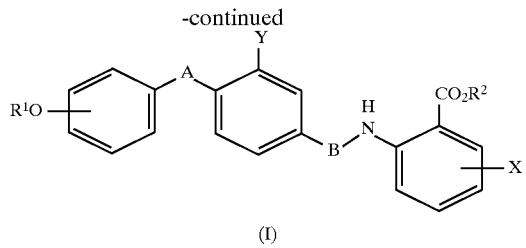

(I)

In the above formulae, $R^1$, $R^2$, B, X and Y are as defined above. There is no limitation to the process for producing the carboxylic acid compound of the formula (II). The carboxylic acid compound may be one produced by any of conventional processes and thus is usually obtained by a coupling reaction of two benzene derivatives. In this case, one of the characteristics of the compounds of the formula (I) and of the synthesis of the compounds of the formula (I) is that the benzene derivatives which are easily available and cheap can be employed as starting materials.

The condensation reaction of the carboxylic acid compounds of the formula (II) with the aniline compounds of the formula (III) can be carried out in accordance with conventional methods. The known condensation methods include a method having an acid halide compound-preparation step and other methods having no acid halide compound-preparation step.

In the condensation method having the acid halide compound-preparation step, the carboxylic acid compound of the formula (II) is reacted with a hologenation agent, for example, oxalyl chloride or thionyl chloride in the presence or non-presence of an additive, for example, DMF, to convert the carboxylic acid compound to a corresponding carboxylic acid halide compound, and then the acid halide compound is further condensation-reacted with the aniline compound of the formula (III) in the presence or non-presence of a base, to obtain the compound of the formula (I).

Also, in the condensation method having no acid halide compound-preparation step, the carboxylic acid compound of the formula (II) is activated with one of various activating agents, for example, mixed acid anhydride, carbodiimides, imidazolating agents, halophosphoric acid esters and cyanophosphoric acid esters, and the resultant-compound is reacted with the aniline compound of the formula (III), thereby to obtain the compound of the formula (I).

In the benzene derivatives of the formula (I) of the present invention, when the $R^1O$— group is a hydroxyl group, the benzene derivatives can be produced by, for example, the following scheme: Namely, a carboxylic acid compound represented by the formula (IV) in which formula (IV), $R^5O$— represents a substituent in which a hydroxyl group (HO— group) is protected by a certain protective treatment, is condensation-reacted with an aniline derivative of the formula (V), to synthesize a compound of the formula (VI), and then a removal treatment for the protection is applied to the compound of the formula (VI) to provide a target compound of the formula (I) in which —$OR^1$ is a —OH group).

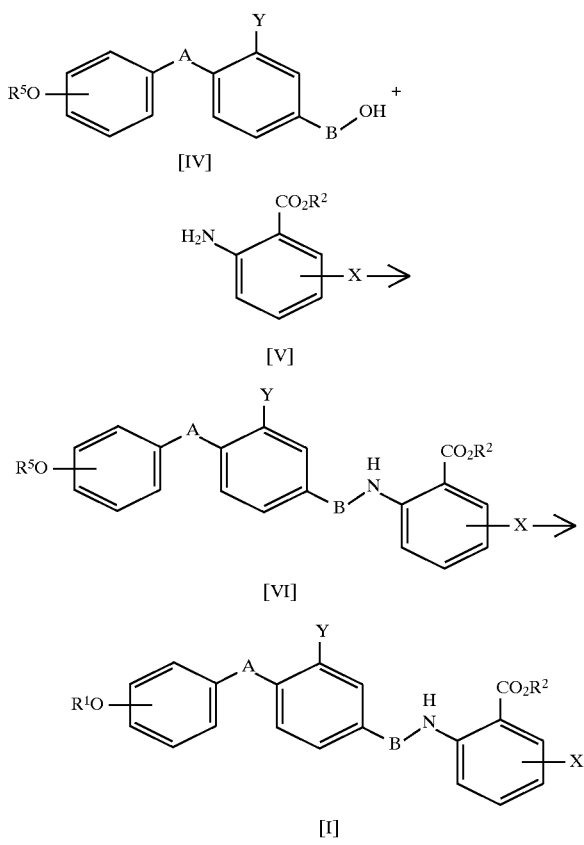

In the above formulae, $R^1$, $R^{2-}$, A, B, X and Y are as defined above, and —$OR^5$ represents an non-active substituent formed by applying a protective treatment to a hydroxyl group.

Examples of typical combination of the protective treatment with the protection-removal treatment include a methylation treatment for the hydroxyl group with a protection-removal treatment for the methylated hydroxy group with $Me_3SiI$, EtSiNa or $BBr_3$; an allyloxidation treatment for the hydroxyl group with a protection-removal treatment using a palladium catalyst; and a benzyloxidation treatment with a protection removal treatment by a hydrogenation. There is no limitation to the method of preparing the protection-treated carboxylic acid compound of the formula (IV) and thus the compound can be produced by any conventional method.

The condensation of the compound of the formula (IV) with the compound of the formula (V) can be effected by the same method as that for the condensation of the compound of the formula (II) with the compound of the formula (III).

Further, in the resultant compound of the formula (I) (in which —$OR^1$=—OH), a hydrogen atom in the hydroxyl group can be converted to a desired substituent, namely, an alkyl group, aralkyl group or alkenyl group as defined in the formula (I), by applying an alkylation, aralkylation or alkenylation reaction thereto. In the conversion reaction, a halide compound corresponding to the desired substituent is used and reacted with the hydroxyl group in the presence or non-presence of a base. In another method, in place of the conversion reaction with the halide compound, the —OH group is reacted with an alcohol ($R^1$—OH) corresponding to the alkyl, aralkyl or alkenyl group as defined in the formula (I), triphenylphosphine and an azodicarboxylic diester.

In the benzene derivatives of the formula (I) of the present invention, when $R^2$ is a $C_1$ to $C_4$ lower alkyl group, the alkyl group can be converted to a hydrogen atom by applying hydrolysis to the benzene derivatives under an acid or basic condition, if necessary.

Further, the benzene derivatives of the formula (I) wherein $R^1$=H of the present invention are optionally converted to pharmacologically acceptable salts thereof, and the benzene derivatives of the formula (I) wherein $R^2$=H or a $C_1$–$C_4$ alkyl group and salts thereof are optionally converted to pharmacologically acceptable solvates thereof.

The benzene derivatives, pharmacologically acceptable salts thereof, and pharmacologically acceptable solvents of the benzene derivatives and salts thereof, of the present invention are used, together with a desired amount of pharmaceutically acceptable carriers, to provide pharmaceutical compositions, and the pharmaceutical compositions can be dosed by oral dosage methods; non-oral dosage methods, for example, phleboclysis, hypodermic or intramuscular injection, percutaneous dosage, intrarectal dosage, intranasal dosage, or instillation; or inhalation.

The carriers as mentioned above include all the additives capable of being mixed and used together with the benzene derivatives of the formula (I), the salts thereof and solvates of the benzene derivatives and salts thereof, and which are pharmacologically acceptable.

The form of the pharmaceutical compositions for the oral medications includes tablets, pills, granules, powders, liquids, suspensions, syrups, capsules, etc.

To provide the tablets, a desired pharmaceutical composition is formed by a conventional forming method using an excipient, for example, lactose, starch, crystalline cellulose, etc., a binder, for example, carboxymethyl cellulose, methyl cellulose, polyvinylpyrrolidone, etc., and a disintegrator, for example, sodium alginate, sodium hydrogen carbonate, sodium laurylsulfate, etc.

The pills, granules and powders can be formed by the conventional forming method using the excipient and others as mentioned above.

The liquids, suspensions and syrups can be prepared by mixing, to the desired compositions, glycerol esters, for example, tricaprylin, and triacetin; alcohols for example, ethyl alcohol; water; or vegetable oils, for example, corn oil, cotton seed oil, coconut oil, almond oil, peanut oil and olive oil.

The capsules can be formed by packing the granules, powders or liquids of the desired pharmaceutical compositions in capsules made from, for example, gelatin.

The forms of the medicines for the phleboclysis, hypodermic and intramuscular dosages are injections which are in the form of a sterilized aqueous or non-aqueous solution. In the aqueous solution, for example, a physiological saline is used as a solvent. In the non-aqueous solution, for example, propyleneglycols, polyethylene glycols, vegetable oils such as olive oil, and organic esters such as ethyl oleate which are acceptable for injection, are used as a solvent. These medicines are optionally added with a tonicity balancer, disinfectant, wetting agent, emulsifier, dispersant and stabilizer, and can be sterilized by filtration through a bacteria-retaining filter, addition of a sterilizing agent, heating, and irradiation in an appropriate manner. Also, a sterilized solid medicine may be prepared, and just before the use, the solid medicine may be dissolved in a sterilized water or sterilized solvent for injection, and the solution may be used.

The medicines for the percutaneous dosage may be in the form of an ointment or cream. The ointment can be prepared by the conventional methods by using an oil, for example, caster oil and olive oil; or a vaseline. The creams can be prepared by the conventional methods by using a fatty oil;

diethyleneglycol; or an emulsifier, for example, sorbitan monofatty acid ester.

For the intrarectal dosage, usual suppositories, for example, in the form of gelatin soft capsules, are used.

The medicines for the intranasal dosage are supplied in the form of a liquid or powdery composition. As a base for the liquid intranasal medicines, water, saline solution, phosphate buffer, and acetate buffer are used. The base may further comprise a surfactant, antioxidant, stabilizer, preserver, and/or viscosity-importing agent. As a base for the powdery intranasal medicines, a water-absorbent base is preferred. For example, the water-absorbent base includes, for example, water-soluble polyacrylic salts, for example, sodium polyacrylate, potassium polyacrylate and ammonium polyacrylate; cellulose-lower alkyl ethers, for example, methyl cellulose, hydroxyethyl cellulose, hydroxypropyl cellulose and sodium carboxymethylcellulose; polyethylene glycols; polyvinylpyrrolidons; amylose; pluran; cellulose compounds, for example, water-insoluble crystalline cellulose, a-cellulose and cross-linked sodium carboxymethylcellulose; starch compounds, for example, hydroxypropylstarch, carboxymethylstarch, cross-linked starches, amylose, amylopectin, and pectin; proteins, for example, gelatin, casein and sodium caseinate; gums, for example, gum arabi, tragacanth gum and glucomannan gum; polyvinylpolypyrrolidone; cross-linked vinyl polymers, for example, cross-linked polyacrylic acids and salts thereof, cross-linked polyvinyl alcohols, and cross-linked polyhydroxyethyl methacrylate. These compounds may be used alone or in mixtures of two or more thereof. The medicines for the powdery intranasal dosage may further comprise an antioxidant, coloring agent, preservative, disinfectant and antiseptic. These liquid and powdery medicines for the intranasal dosage can be dosed by using a spraying device.

The ophthalmic solutions for instillation may be in the form of an aqueous solution or a non-aqueous solution. In the aqueous ophthalmic solutions, the solvent may be a sterilized purified water, physiological saline solution, or other appropriate aqueous solvent. The aqueous ophthalmic solutions for instillation include aqueous ophthalmic solutions containing, as an aqueous solvent, a sterilized purified water alone; viscous ophthalmic solutions containing, in addition to the aqueous solvent, a viscosity-imparting agent, for example, carboxymethylcellulose, methylcellulose, hydroxypropylcellulose, or polyvinylpyrrolidone; an aqueous ophthalmic suspension containing, in addition to the aqueous solvent, a suspending agent, for example, a surfactant or a polymeric thickener; and solubilized ophthalmic solution containing, in addition to the aqueous solvent, a stabilizing agent, for example, a nonionic surfactant. The non-aqueous ophthalmic solution contains a non-aqueous solvent as a solvent for the instillation. The non-aqueous ophthalmic solutions include non-aqueous ophthalmic solutions containing, as a non-aqueous solvent, a vegetable oil, liquid paraffin, mineral oil or propylene glycol; and non-aqueous ophthalmic suspensions in which active ingredients are suspended by a thixotropic colloidal material, for example, aluminum monostearate added to the non-aqueous solvent. These medicines may optionally contain a tonicity balancer, a preservative, a buffer, an emulsifier, and a stabilizer. The medicines can be sterilized by applying filtration through a bacteria-retaining filter, addition of a sterilizing agent, heating or an irradiation treatment. Also, the above-mentioned medicine may be prepared by sterilizing a solid medicine, and just before the use, dissolving or suspending the sterized solid medicine in a sterilized solution, and then used.

The form of the medicines for instillation, except for the ophthalmic medicines, includes ointments for instillation, including vaseline; liniments containing a diluted iodine tincture solution, zinc sulfate solution, methylrosalinine chloride; epipastic consisting of a fine powder of the active ingredients which is directly dosed; and inserting medicine in which active ingredients are mixed or impregnated in an appropriate base or material, and which is inserted into palpebras.

Also, for the inhalation, a solution or suspension liquid containing an active ingredient and a usual excipient for medicine is used.

For example, the solution or suspension is used for an aerosol spray. Also, dry powdery active ingredients can be dosed through an inhalator or other apparatus so that the active ingredients are brought into direct contact with the lungs.

The pharmaceutical compositions of the present invention as described above are characterized by exhibiting an IgE antibody production-inhibiting performance and are effective as therapeutic medicines for allergic diseases.

Therefore, prophlactic or therpeutic medicines for the allergic diseases are provided by the present invention. The medicines comprise, as active ingredients, the benzene derivatives, the pharmacologically acceptable salts thereof and the pharmacologically acceptable solvates of the benzene derivatives and the salts thereof, of the present invention, and exhibit an excellent IgE antibody production-inhibiting performance.

The dose of the medicines comprising the benzene derivatives of the formula (I) of the present invention is appropriately established in consideration of the type of the disease, the route of the medication and the conditions, age, sex, and weight of the patient. In the case of oral dosage, the dose is about 0.1 to 1000 mg per day per person, preferably 1 to 300 mg/day/person, and in the case of non-oral dosage, for example, phleboclysis, hypodermic, intramuscular, percutaneous, intrarectal, intranasal, instillation or inhalation dosage, the dose is about 0.1 to 100 mg/day/person, preferably 0.1 to 30 mg/day/person. The medicine is preferably prepared so as to meet the above dosage amount. When the compounds of the present invention are used as prophylactic medicines, there is no limitation to the medication methods and the compounds can be dosed by known methods for the usual prophylactic medicines.

The compounds of the present invention exhibit the production of IgE antibodies in human lymphocytes, for example, exposed to non-specific antigen stimuli (IL-4+IL-10 (interleukin 10)+anti CD 40 Ab (anti CD 40 antibody), to a concentration at which no cytoloxity is exhibited, as concretely described in the examples later. Accordingly, the compounds of the present invention are useful for prophylactic or therapeutic medicines for allergic diseases derived from the IgE antibody production, for example, bronchial asthma, allergic shinitis, allergic conjunctivitis, atopic dermatitis, anaphylactic shocks, mite allergy, pollinosis, food allergy, urticaria, ulcerative gastroenteritis, eosinophilic gastroenteritis and medicamentosus exanthema.

Among these allergic diseases, the pharmaceutical compositions of the present invention are effective for the bronchial asthma, allergic rhinitis, allergic conjunctivitis, atopic dermatitis, anaphylactic shocks, mite allergy, pollinosis and food allergy.

The compounds of the present invention exhibit an inhibiting performance against the IgE antibody production. Thus, the compounds of the present invention can inhibit undesirable immune reactions which cause the allergic diseases, and therefore are useful as prophylactic and/or therapeutic medicines for the allergic diseases.

EXAMPLES

The present invention will be explained in detail by the referential examples and examples. However, these examples do not limit the scope of the present invention in any way.

Referential Example 1

Synthesis of 4-(4-benzyloxyphenoxy)phenylacetic acid

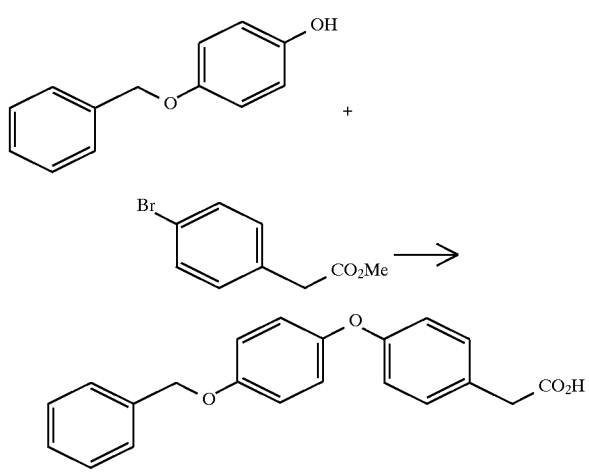

To hydroquinone monobenzylether (8.01 g, 40 mmole), benzene (100 ml) and methyl alcohol (25 ml) were added, and then a 28% sodium methylate solution (7.3 ml, 38 mmole) was gradually added dropwise, and the resultant mixture was agitated at room temperature for one hour. The resultant reaction liquid was concentrated, and then mixed with methyl 4-bromophenylacetate (9.16 g, 40 mmole) and copper (I) chloride (CuCl, 1.25 g, 12 mmole). The resultant mixture was heat-agitated at a temperature of 120° C. for 30 hours. The resultant reaction mixture was neutralized with hydrochloric acid, the reaction product was extracted with ethyl acetate, and the resultant extract was concentrated and dried. The resultant concentrate was purified by a silica gel chromatography. A target methyl ester was obtained in an amount of 4.73 g, 13.7 mmole. The yield thereof was 36%.

The methyl ester compound (4.76 g, 13.7 mmole) was dissolved in THF (10 ml), and the resultant solution was added with methyl alcohol (5 ml) and a 4-N aqueous lithium hydroxide solution (5 ml). The resultant reaction mixture was agitated at room temperature for 4 hours. After the reaction completed, the resultant reaction liquid was neutralized with hydrochloric acid and concentrated until the liquid volume became one half of the original volume. The resultant crystals were collected by filtration and dried. The target compound (4.31 g, 12.9 mmole) was obtained. The yield was 94%.

Example 1

Synthesis of methyl 2-(4-(4-benzyloxyphenoxy) phenylacetamido)benzoate (Compound No. 3)

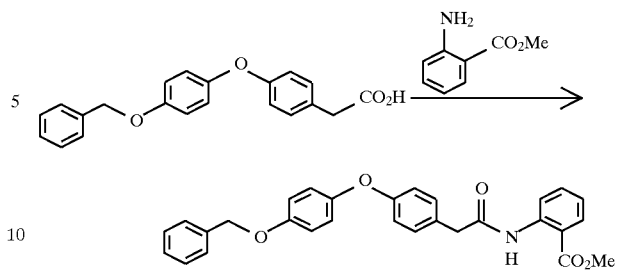

In a nitrogen gas atmosphere, the methyl 4-(4-benzyloxyphenoxy)phenylacetate (4.30 g, 12.9 mmole) prepared in Referential Example 1 was mixed with methylene chloride (70 ml), then with oxalyl chloride (2.13 g, 16.8 mmole), and the resultant reaction mixture was agitated at a temperature of 50° C. for 3 hours. The obtained reaction liquid was concentrated, and the concentrate was dissolved in a dry methylene chloride (60 ml). The resultant solution was cooled with ice, mixed with methyl benzoate (1.80 g, 12.3 mmole) and then with trimethylamine (1.80 g, 18.1 mmole), and the resultant mixture was agitated at a temperature of 50° C. for one hour and then at room temperature for one night. The resultant reaction liquid was washed with water, the reaction product was extracted with ethyl acetate, and the extract was dried and concentrated. The concentrate was purified with silica gel chromatography. A target compound (4.29 g, 9.2 mmole) was obtained. The yield was 75%.

The NMR measurement results of the compound is shown below.

$^1$H-NMR(CDCl$_3$): δ3.72(2H, s), 3.87(3H, s), 5.04(2H, s), 6.91–7.02(6H, m), 7.06(1H, td, J=8.6 Hz, 1.6 Hz), 7.24–7.46 (7H, m), 7.52(1H, td, J=8.0 Hz, 1.6 Hz), 7.99(1H, dd, J=8.2 Hz, 1.6 Hz), 8.71(1H, dd, J=8.6 Hz, 1.3 Hz), 11.03(1H, brs)

Example 2

The compounds shown in Table 1 (Compound No. 1, No. 33, No. 36, No. 38 and No. 45) were synthesized by the similar procedures to in Example 1. Table 1 also shows the yields and NMR measurement results of the compounds.

TABLE 1

| Compound No. | Yield (%) | $^1$H-NMR (CDCl$_3$):δ |
|---|---|---|
| 1 | 63 | 3.74 (2 H, s), 3.85 (3 H, s), 4.03 (2 H, s), 6.91 (2 H, d, J = 8.57 Hz), 7.00 (2 H, d, J = 8.58 Hz), 7.06 (1 H, ddd, J = 0.99, 7.25, 7.92 Hz), 7.19–7.26 (7 H, m), 7.34 (2 H, d, J = 8.25 Hz), 7.52 (1 H, ddd, J = 1.32, 7.26, 8.57 Hz), 7.99 (1 H, dd, J = 1.32, 7.91 Hz), 8.72 (1 H, d, J = 8.58 Hz), 11.05 (1 H, br). |
| 33 | 46 | 3.74 (2 H, s), 3.84 (3 H, s), 5.02 (2 H, s), 6.62–6.74 (3 H, m), 7.03 (2 H, d, J = 8.6 Hz), 7.21 (1 H, t, J = 8.2 Hz), 7.32 (2 H, d, J = 8.6 Hz), 7.37–7.40 (5 H, m), 7.47 (1 H, dd, J = 8.9 and 2.6 Hz), 7.95 (1 H, d, J = 2.6 Hz), 8.72 (1 H, d, J = 8.9 Hz), 10.95 (1 H, sbr). |
| 36 | 55 | 3.75 (2 H, s), 3.84 (3 H, s), 5.02 (2 H, s), 6.61–6.78 (4 H, m), 7.03 (2 H, d, J = 8.6 Hz), 7.20 (1 H, t, J = 8.2 Hz), 7.33 (2 H, d, |

TABLE 1-continued

| Compound No. | Yield (%) | $^1$H-NMR (CDCl$_3$):δ |
|---|---|---|
| | | J = 8.3 Hz), 7.33–7.38 (5 H, m), 7.97–8.03 (1 H, m), 8.56 (1 H, dd, J = 11.9 and 2.6 Hz). |
| 38 | 47 | 2.31 (3 H, s), 3.73 (2 H, s), 3.83 (3 H, s), 5.01 (2 H, s), 6.61–6.73 (3 H, m), 7.02 (2 H, d, J = 8.6 Hz), 7.20 (1 H, t, J = 8.2 Hz), 7.31–7.41 (8 H, m), 7.78 (1 H, d, J = 2.0 Hz), 8.60 (1 H, d, J = 8.6 Hz), 10.93 (1 H, sbr). |
| 44 | 89 | 3.72 (2 H, s), 3.81 (3 H, s), 5.07 (2 H, s), 6.88–7.10 (7 H, m), 7.14–7.28 (5 H, m), 7.31 (2 H, d, J = 8.25 Hz), 7.50 (1 H, ddd, J = 1.65, 7.26, 8.58 Hz), 7.97 (1 H, dd, J = 1.65, 7.92 Hz), 8.72 (1 H, d, J = 8.25 Hz), 11.04 (1 H, s). |

Example 3

Synthesis of 2-(4-(4-benzyloxyphenoxy) phenylacetamido) benzoic acid (Compound No. 4)

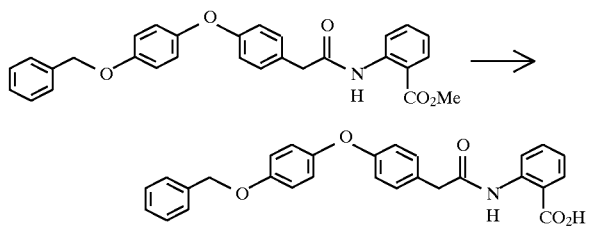

Methyl 4-(4-benzyloxyphenoxy) phenylacetamidobenzoate (278 mg, 0.59 mmole) prepared by the same procedures as in Example 1 was dissolved in THF (5 ml), the resultant solution was mixed with methyl alcohol (5 ml) and an aqueous 4N-lithium hydroxide solution (ml) and stirred at room temperature for 2 hours. After the reaction completed, the obtained reaction liquid was neutralized with hydrochloric acid, and then concentrated to such an extent that the liquid amount was reduced to one half of the original amount. The crystals generated in the concentrate are collected by filtration and dried. Further, the crystals were recrystallized from acetonitrile, to obtain target compound (130 mg, 0.29 mmole). The yield was 49%.

$^1$H-NMR(CDC13): δ3.74(2H, s), 5.00(2H, s), 6.87–6.99 (6H, m), 7.08(1H, t, J=7.5 Hz), 7.24–7.43(7H, m), 7.57(1H, t, J=7.5 Hz), 8.07(1H, d, J=8.0 Hz), 8.75(1H, d, J=8.0 Hz), 10.77(1H, brs).

Example 4

Synthesis of methyl 2-(4-(4-hydroxyphenoxy phenylacetamido)benzoate (Compound No. 5)

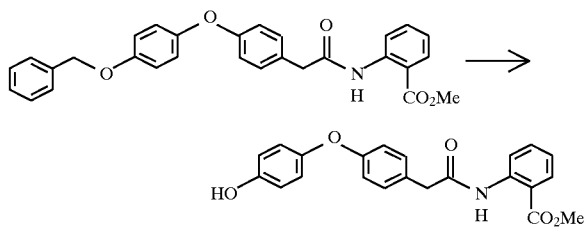

In a nitrogen gas atmosphere, methyl 2-(4-(4-benzyloxyphenoxy)phenylacetamido)benzoate (4.20 g, 9.0 mmole) prepared by the same procedures as in Example 1 was dissolved in ethyl acetate (17 ml), the resultant solution was mixed with a 10% palladium carbon (800 mg) to provide a reaction mixture. After the nitrogen gas is replaced by a hydrogen gas, the reaction mixture was agitated at room temperature for 32 hours. The resultant reaction mixture was filtered through a celite sheet and concentrated. The obtained concentrate was recrystallized from ethyl acetate. The target compound (2.26 g, 6.0 mmole) was obtained at an yield of 66%.

$^1$ H-NMR(DMSO-d6): δ3.70(2H, s), 3.78(3H, s), 6.76 (2H, d, J=8.9 Hz), 6.88(4H, d-like, J=8.6 Hz), 7.18(1H, t, J=7.5 Hz), 7.30(2H, d, J=8.6 Hz), 7.59(1H, t, J=7.8 Hz), 7.89(1H, dd, J=7.9 Hz, 1.7 Hz), 8.29(1H, d, J=7.6 Hz), 9.31(1H, s), 10.61(1H, brs).

Example 5

Compound No. 29 was synthesized by the same procedures as in Example 4. The yield was 93%.

$^1$H-NMR(CDC13): δ3.98(s, 3H), 6.92(d, 2H, J=8.91 Hz), 7.01–7.15(m, 4H), 7.32(t, 1H, J=8.24 Hz), 7.76(t, 1H, J=8.56 Hz), 8.02(d, 2H, J=8.59 Hz), 8.10(dd, 1H, J=1.32, 7.91 Hz), 8.65(d, 1H, J=8.26 Hz), 9.57(s, 1H), 11.63(s, 1H).

Example 6

Synthesis of methyl 2-(4-(4-cyclohexyoxyphenoxy) phenylacetamido)benzoate (Compound No. 7)

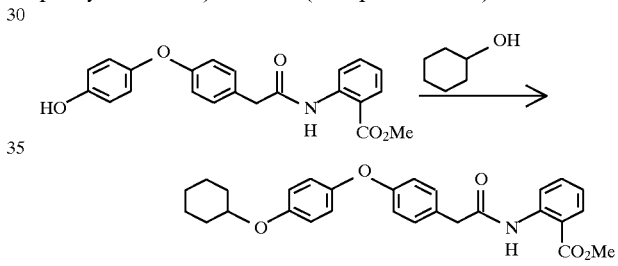

In a nitrogen gas atmosphere, a solution of methyl 2-(4-(4-hydroxyphenoxy)ph-phenylacetamido)benzoate prepared by the same procedures as in Example 4 in N-methylmorpholine (4 ml) was mixed with triphenylphosphine (350 mg, 1.3 mmole), cyclohexanol (0.13 ml, 1.3 mmole) and diethyl azodicarboxylate (230 mg, 1.3 mmole), and then agitated at room temperature for 2 hours. To the resultant mixture, triphenylphosphine (350 mg, 1.3 mmole) cyclohexanol (0.13 ml, 13 mmole), and diethyl azodicarboxylate (230 mg, 1.3 mmole) were added, and the resultant mixed liquid was stirred at room temperature for 2 hours. After the etherizing reaction completed, a white precipitate formed in the resultant reaction mixture was removed by filtration, the filtrate was refined by a silica gel column chromatography. The target compound (241 mg, 0.53 mmole) was obtained with a yield of 81%.

$^1$H-NMR(CDC13): δ1.1–1.6(6H, m), 1.79–1.84(2H, br m), 1.96–2.04(2H, m br), 3.72(2H, s), 3.87(3H, s), 4.10–4.19(1H, m), 6.86(2H, d, J=9.2 Hz), 6.96(4H, d, J=8.3 Hz), 7.06(1H, t, J=8.3 Hz), 7.30(2H, d, J=8.6 Hz), 7.52(1H, td, J=8.6 Hz, 1.7 Hz), 7.99(1H, dd, J=8.3 Hz, 1.7 Hz), 8.71(1H, dd, J=8.6 Hz, 1.0 Hz), 11.03(1H, br s).

Example 7

Synthesis of 2-(4-(4-cyclohexyloxyphenoxy) phenylacetamido)benzoic acid (Compound No. 8)

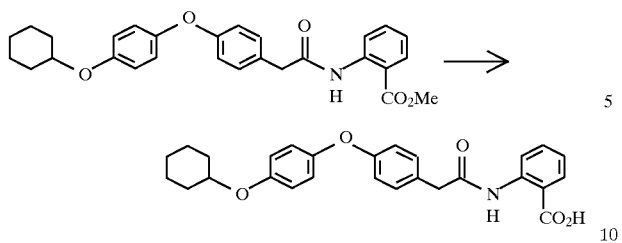

Methyl 2-(4-(4-cyclohexyloxyphenoxy)phenylacetamido)benzoate (240 mg, 0.53 mmole) prepared in the same manner as in Example 6 was dissolved in THF (8 ml), the solution was mixed with methyl alcohol (5 ml) and an aqueous 4N-lithium hydroxide solution (2 ml), and the resultant reaction mixture was agitated at room temperature for 3 hours. After a hydrolysis reaction completed, the resultant reaction liquid was neutralized with hydrochloric acid, and concentrated until the liquid amount reduced to a half of the original amount. From the concentrate, the reaction product was extracted with ethyl acetate and the obtained extract solution was dried and concentrated. The resultant oily concentrate was recrystallized from acetonitrile. The target compound (121 mg) was obtained with a yield of 51%.

$^1$H-NMR(DMSO-d6): δ1.24–1.55(6H, m), 1.65–1.75(2H, br m), 1.85–1.95(2H, br m), 3.72(2H, s), 4.20–4.28(1H, m), 6.89–6.96(6H, m), 7.13(1H, t, J=8.5 Hz), 7.32(2H, d, J=8.6 Hz), 7.56(1H, t, J=8.0 Hz), 7.95(1H, dd, J=7.9 Hz, 1.7 Hz), 8.51(1H, d, J=8.3 Hz), 11.16(1H, sbr).

Example 8

The compound shown in Tables 2 to 5 were synthesized in accordance with the similar procedures to in Example 6.

The yield of each compound was calculated based on the molar amount of the corresponding starting hydroxyl compound ($R^1$O=OH, $R^1$ is as defined above).

TABLE 2

| Compound No. | Yield (%) | $^1$H-NMR (CDCl$_3$):δ |
|---|---|---|
| 11 | 94 | 1.56–1.68 (m, 2 H), 1.76–1.88 (m, 6 H), 3.72 (s, 2 H), 3.87 (s, 3 H), 4.70 (brm, 1 H), 6.83 (d, 2 H, J = 8.9 Hz), 6.96 (d, 2 H, J = 8.6 Hz), 6.97 (d, 2 H, J = 8.9 Hz), 7.05 (ddd, 1 H, J = 7.9 Hz, 6.9 Hz, 1.0 Hz), 7.30 (d, 2 H, J = 8.6 Hz), 7.51 (ddd, 1 H, J = 8.6 Hz, 6.9 Hz, 1.3 Hz), 7.98 (dd, 1 H, J = 7.9 Hz, 1.3 Hz), 8.72 (dd, 1 H, J = 8.6 Hz, 1.0 Hz), 11.03 (brs, 1 H). |
| 13 | 85 | 1.5–1.7 (8 H, br), 1.77–1.95 (6 H, mbr), 3.72 (2 H, s), 3.87 (3 H, s), 4.34 (1 H, m), 6.82 (2 H, d, J = 8.9 Hz), 6.96 (4 H, d, J = 7.9 Hz), 7.06 (1 H, t, J = 8.4 Hz), 7.30 (2 H, d, J = 8.6 Hz), 7.52 (1 H, t, J = 8.2 Hz), 7.99 (1 H, dd, J = 7.9 Hz, 1.5 Hz), 8.72 (1 H, dd, J = 8.2 Hz, 1.0 Hz), 11.03 (1 H, br). |
| 15 | 47 | 1.28–1.48 (m, 16 H), 1.58–1.81 (m, 4 H), 2.02–2.14 (m, 2 H), 3.72 (s, 2 H), 3.86 (s, 3 H), 4.34 (m, 1 H), 6.84 (d, 2 H, J = 9.2 Hz), 6.96 (d, 2 H, J = 9.2 Hz), 6.97 (d, 2 H, |

TABLE 2-continued

| Compound No. | Yield (%) | $^1$H-NMR (CDCl$_3$):δ |
|---|---|---|
| | | J = 8.6 Hz), 7.05 (ddd, 1 H, J = 7.9 Hz, 6.9 Hz, 1.0 Hz), 7.30 (d, 2 H, J = 8.6 Hz), 7.51 (ddd, 1 H, J = 8.6 Hz, 6.9 Hz, 1.7 Hz), 7.98 (dd, 1 H, J = 7.9 Hz, 1.7 Hz), 8.72 (d, 1 H, J = 8.6 Hz), 11.03 (s, 1 H). |
| 17 | 72 | 1.32 (d, 6 H, J = 6.3 Hz), 3.72 (s, 2 H), 3.87 (s, 3 H), 4.47 (sep, 1 H, J = 6.3 Hz), 6.84 (d, 2 H, J = 8.9 Hz), 6.96 (d, 2 H, J = 8.6 Hz), 6.97 (d, 2 H, J = 8.9 Hz), 7.06 (ddd, 1 H, J = 8.2 Hz, 6.9 Hz, 1.0 Hz), 7.30 (d, 2 H, J = 8.6 Hz), 7.51 (ddd, 1 H, J = 8.6 Hz, 6.9 Hz, 1.7 Hz), 7.98 (dd, 1 H, J = 8.2 Hz, 1.7 Hz), 8.72 (dd, 1 H, J = 8.6 Hz, 1.0 Hz), 11.03 (s, 1 H). |

TABLE 3

| Compound No. | Yield (%) | $^1$H-NMR (CDCl$_3$):δ |
|---|---|---|
| 19 | 50 | 0.96 (t, 6 H, J = 7.6 Hz), 1.67 (dq, 4 H, J = 7.6 Hz, 5.9 Hz), 3.72 (s, 2 H), 3.86 (s, 3 H), 4.03 (quint, 1 H, J = 5.9 Hz), 6.85 (d, 2 H, J = 9.2 Hz), 6.94–6.99 (m, 4 H), 7.05 (ddd, 1 H, J = 7.9 Hz, 6.9 Hz, 1.0 Hz), 7.30 (d, 2 H, J = 8.6 Hz), 7.51 (ddd, 1 H, J = 8.6 Hz, 6.9 Hz, 1.7 Hz), 7.98 (dd, 1 H, J = 7.9 Hz, 1.7 Hz), 8.72 (dd, 1 H, J = 8.6 Hz, 1.0 Hz), 11.03 (s, 1 H). |
| 21 | 82 | 1.5–1.7 (8 H, m), 1.77–1.95 (6 H, mbr), 3.95 (3 H, s), 4.38 (1 H, m), 6.88 (2 H, d, J = 8.9 Hz), 6.98–7.04 (4 H, m), 7.11 (1 H, t, J = 7.7 Hz), 7.60 (1 H, td, J = 7.6 Hz, 1.6 Hz), 8.00 (2 H, d, J = 8.9 Hz), 8.07 (1 H, dd, J = 7.9 Hz, 1.7 Hz), 8.92 (1 H, dd, J = 8.6 Hz, 0.7 Hz), 11.98 (1 H, sbr). |
| 31 | 85 | 1.51–1.74 (8 H, mbr), 1.76–2.00 (6 H, mbr), 3.96 (3 H, s), 4.40 (1 H, quint, J = 4.0 Hz), 6.91 (2 H, d, J = 8.9 Hz), 7.00–7.06 (3 H, m), 7.15 (1 H, td, J = 7.6 and 1.3 Hz), 7.62 (1 H, td, J = 7.6 and 1.3 Hz), 8.07–8.12 (2 H, m), 8.63 (1 H, d, J = 2.3 Hz), 8.86 (1 H, d, J = 8.0 Hz), 12.15 (1 H, sbr). |
| 40 | 44 | 1.4–1.6 (8 H, m), 1.72–1.95 (6 H, m), 2.31 (3 H, s), 3.71 (2 H, s), 3.86 (3 H, s), 4.34 (1 H, quint, J = 4.0 Hz), 6.81 (2 H, d, J = 8.9 Hz), 6.94–6.98 (4 H, m), 7.30 (2 H, d, J = 8.9 Hz), 7.34 (1 H, m), 7.79 (1 H, d, J = 1.7 Hz), 8.59 (1 H, d, J = 8.6 Hz), 10.90 (1 H, sbr). |

TABLE 4

| Compound No. | Yield (%) | $^1$H-NMR (CDCl$_3$):δ |
|---|---|---|
| 42 | 46 | 1.02 (6 H, d, J = 6.6 Hz), 2.07 (1 H, quint, J = 6.6 Hz), 3.69 (2 H, d, J = 6.6 Hz), 3.72 (2 H, s), |

TABLE 4-continued

| Compound No. | Yield (%) | $^1$H-NMR (CDCl$_3$):δ |
|---|---|---|
| | | 3.88 (3 H, s), 6.86 (2 H, d, J = 9.2 Hz), 6.95 (2 H, d, J = 7.9 Hz), 6.98 (2 H, d, J = 8.9 Hz), 7.06 (1 H, td, J = 7.7 and 1.0 Hz), 7.29 (2 H, t, J = 8.0 Hz), 7.52 (1 H, td, J = 7.9 and 1.6 Hz), 7.99 (1 H, dd, J = 7.9 and 1.6 Hz), 8.71 (1 H, d, J = 7.9 Hz). |
| 47 | 69 | 1.23–1.92 (14 H, m), 3.71 (2 H, s), 3.87 (3 H, s), 4.35 (1 H, tt, J = 3.96, 7.92 Hz), 6.86–6.97 (4 H, m), 7.02–7.11 (3 H, m), 7.28 (2 H, m), 7.51 (1 H, ddd, J = 1.65, 7.26, 8.57 Hz), 7.98 (1 H, dd, J = 1.65, 7.91 Hz), 8.70 (1 H, dd, J = 0.99, 8.58 Hz), 11.3 (1 H, s). |
| 48 | 68 | 3.72 (2 H, s), 3.87 (3 H, s), 4.31 (4 H, s), 6.90–7.02 (10 H, m), 7.06 (1 H, ddd, J = 8.2 Hz, 7.3 Hz, and 1.0 Hz), 7.25–7.33 (4 H, m), 7.52 (1 H, ddd, J = 8.6 Hz, 7.3 Hz and 1.7 Hz), 7.99 (1 H, dd, J = 8.2 Hz, and 1.7 Hz), 8.71 (1 H, dd, J = 8.6 Hz, and 1.0 Hz), 11.04 (1 H, brs). |
| 50 | 52 | 2.52 (1 H, ddd, J = 6.9 Hz, 6.6 Hz, and 1.3 Hz), 2.55 (1 H, ddd, J = 6.9 Hz, 6.9 Hz, and 1.3 Hz), 3.72 (2 H, s), 3.87 (3 H, s), 3.99 (2 H, t, J = 6.9 Hz), 5.11 (1 H, dd, J = 10.2 Hz, and 1.7 Hz), 5.17 (1 H, dd, J = 17.1 Hz, and 1.7 Hz), 5.90 (1 H, dddd, J = 17.1 Hz, 10.2 Hz, 6.9 Hz and 6.6 Hz), 6.86 (2 H, d, J = 8.9 Hz), 6.95 (2 H, d, J = 8.6 Hz), 6.98 (2 H, d, J = 8.9 Hz), 7.06 (1 H, ddd, J = 8.2 Hz, 7.3 Hz, and 1.0 Hz), 7.30 (2 H, d, J = 8.6 Hz), 7.51 (1 H, ddd, J = 8.6 Hz, 7.3 Hz, and 1.3 Hz), 7.98 (1 H, dd, J = 8.2 Hz, and 1.3 Hz), 8.71 (1 H, dd, J = 8.6 Hz, and 1.0 Hz), 11.04 (1 H, brs). |

TABLE 5

| Compound No. | Yield (%) | $^1$H-NMR (CDCl$_3$):δ |
|---|---|---|
| 52 | 41 | 0.93 (6 H, t, J = 7.3 Hz), 1.34–1.55 (4 H, m), 1.62–1.71 (1 H, m), 3.72 (2 H, s), 3.82 (2 H, d, J = 5.6 Hz), 3.87 (3 H, s), 6.86 (2 H, d, J = 8.9 Hz), 6.95 (2 H, d, J = 8.6 Hz), 6.98 (2 H, d, J = 8.9 Hz), 7.06 (1 H, ddd, J = 8.2 Hz, 6.9 Hz, and 1.0 Hz), 7.30 (2 H, d, J = 8.6 Hz), 7.52 (1 H, ddd, J = 8.6 Hz, 6.9 Hz, and 1.3 Hz), 7.99 (1 H, dd, J = 8.2 Hz, and 1.3 Hz), 8.71 (1 H, dd, J = 8.6 Hz, and 1.0 Hz), 11.03 (1 H, brs). |
| 54 | 95 | 0.98 (3 H, t, J = 7.3 Hz), 1.45–1.64 (2 H, m), 1.71–1.82 (2 H, m), 3.72 (2 H, s), 3.87 (3 H, s), 3.93 (2 H, t, J = 6.6 Hz), 6.85 (2 H, d, J = 8.9 Hz), 6.96 (2 H, d, J = 8.6 Hz), 6.98 (2 H, d, J = 8.9 Hz), 7.06 (1 H, ddd, J = 8.2 Hz, 6.9 Hz, and 1.0 Hz), 7.30 (2 H, d, J = 8.6 Hz), 7.52 (1 H, ddd, J = 8.6 Hz, 6.9 Hz, and 1.7 Hz), 7.99 (1 H, dd, J = 8.2 Hz, and 1.3 Hz), 8.71 (1 H, dd, J = 8.6 Hz, and 1.0 Hz), 11.03 (1 H, brs). |

TABLE 5-continued

| Compound No. | Yield (%) | $^1$H-NMR (CDCl$_3$):δ |
|---|---|---|

Example 9

The compounds shown in Tables 6 to 11 were synthesized by the similar procedures to in Example 7. The yield of each compound was calculated based on the molar amount of the corresponding starting methyl ester compound ($R^2$=Me, $R^2$ is as defined above).

TABLE 6

| Compound No. | Yield (%) | $^1$H-NMR (DMSO-d$_6$):δ |
|---|---|---|
| 2 | 78 | 3.74 (2 H, s), 4.16 (2 H, s), 6.93 (2 H, d, J = 8.91 Hz), 6.97 (2 H, d, J = 8.58 Hz), 7.12 (1 H, ddd, J = 1.32, 7.26, 7.92 Hz), 7.19–7.38 (9 H, m), 7.56 (1 H, ddd, J = 1.65, 7.26, 8.58 Hz), 7.94 (1 H, dd, J = 1.65, 7.92 Hz), 8.50 (1 H, dd, J = 0.66, 8.25 Hz), 11.14 (1 H, s), 13.55 (1 H, br). |
| 12 | 66 | 1.53–1.85 (m, 6 H), 1.86–1.92 (m, 2 H), 3.72 (s, 2 H), 4.76 (br, 1 H), 6.88–6.98 (m, 6 H), 7.13 (dd, 1 H, J = 7.9 Hz, 7.6 Hz), 7.32 (d, 2 H, J = 8.6 Hz), 7.57 (ddd, 1 H, J = 8.9 Hz, 7.6 Hz, 1.3 Hz), 7.95 (dd, 1 H, J = 7.9 Hz, 1.3 Hz), 8.50 (d, 1 H, J = 8.9 Hz), 11.16 (s, 1 H). |
| 14 | 80 | 1.5–1.7 (8 H, br), 1.70–1.90 (6 H, mbr), 3.72 (2 H, s), 4.41 (1 H, m), 6.87–6.98 (6 H, m), 7.13 (1 H, t, J = 6.9 Hz), 7.32 (2 H, d, J = 8.6 Hz), 7.58 (1 H, td, J = 7.9 Hz, 1.7 Hz), 7.95 (1 H, dd, J = 7.9 Hz, 1.7 Hz), 8.50 (1 H, d, J = 8.6 Hz), 11.10 (1 H, sbr). |

TABLE 7

| Compound No. | Yield (%) | $^1$H-NMR (DMSO-d$_6$):δ |
|---|---|---|
| 16 | 68 | 1.34–1.72 (m, 22 H), 3.72 (s, 2 H), 4.37 (br, 1 H), 6.91 (d, 2 H, J = 9.2 Hz), 6.92 (d, 2 H, J = 8.6 Hz), 6.96 (d, 2 H, J = 9.2 Hz), 7.13 (dd, 1 H, J = 7.9 Hz, 7.3 Hz), 7.33 (d, 2 H, J = 8.6 Hz), 7.57 (ddd, 1 H, J = 8.6 Hz, 7.3 Hz, 1.7 Hz), 7.95 (dd, 1 H, J = 7.9 Hz, 1.7 Hz), 8.51 (d, 1 H, J = 8.6 Hz), 11.17 (s, 1 H). |
| 18 | 45 | 1.32 (d, 6 H, J = 6.3 Hz), 3.72 (s, 2 H), 3.87 (s, 3 H), 4.47 (sep, 1 H, J = 6.3 Hz), 6.84 (d, 2 H, J = 8.9 Hz), 6.96 (d, 2 H, J = 8.6 Hz), 6.97 (d, 2 H, J = 8.9 Hz), 7.06 (ddd, 1 H, J = 8.2 Hz, 6.9 Hz, 1.0 Hz), 7.51 (ddd, 1 H, J = 8.6 Hz, 6.9 Hz, 1.7 Hz), 7.98 (dd, 1 H, J = 8.2 Hz, 1.7 Hz), 8.72 (dd, 1 H, J = 8.6 Hz, 1.0 Hz), 11.22 (s, 1 H), |

TABLE 7-continued

| Compound No. | Yield (%) | $^1$H-NMR (DMSO-$d_6$):δ |
|---|---|---|
| 20 | 40 | 13.56 (brs, 1 H).<br>0.90 (d, J = 7.3 Hz), 1.60 (dq, 4 H, J = 7.3 Hz, 5.9 Hz), 3.72 (s, 2 H), 4.14 (quint, 1 H, J = 5.9 Hz), 6.91 (d, 2 H, J = 8.6 Hz), 6.94 (s, 4 H), 7.13 (dd, 1 H, J = 7.9 Hz, 7.6 Hz), 7.32 (d, 2 H, J = 8.6 Hz), 7.57 (dd, 1 H, J = 8.6 Hz, 7.9 Hz), 7.95 (d, 1 H, J = 7.6 Hz), 8.50 (d, 1 H, J = 8.6 Hz), 11.14 (s, 1 H). |

TABLE 8

| Compound No. | Yield (%) | $^1$H-NMR (DMSO-$d_6$):δ |
|---|---|---|
| 22 | 78 | 1.5–1.7 (8 H, br), 1.71–2.00 (6 H, mbr), 4.46 (1 H, m), 6.95 (2 H, d, J = 9.2 Hz), 7.05–7.09 (4 H, m), 7.20 (1 H, t, J = 7.7 Hz), 7.66 (1 H, t, J = 8.0 Hz), 7.94 (2 H, d, J = 8.9 Hz), 8.05 (1 H, dd, J = 7.9 Hz, 0.7 Hz), 8.70 (1 H, d, J = 8.6 Hz), 12.13 (1 H, sbr). |
| 28 | 76 | 3.92 (s, 2 H), 6.98 (d, 2 H, J = 9.23 Hz), 7.11–7.00 (m, 4 H), 7.34 (t, 1 H, J = 7.59 Hz), 7.51 (d, 2 H, J = 8.24 Hz), 7.77 (t, 1 H, J = 8.24 Hz), 8.16 (dd, 1 H, J = 1.32, 7.91 Hz), 8.71 (d, 1 H, J = 8.24 Hz), 9.53 (s, 1 H), 11.34 (s, 1 H), 13.77 (br, 1 H). |
| 30 | 78 | 6.92 (d, 2 H, J = 8.89 Hz), 7.14–7.06 (m, 4 H), 7.28 (t, 1 H, J = 7.59 Hz), 7.74 (t, 1 H, J = 8.26 Hz), 8.02 (d, 2 H, J = 8.59 Hz), 8.14 (dd, 1 H, J = 1.32, 7.91 Hz), 8.78 (d, 1 H, J = 8.26 Hz), 9.56 (s, 1 H), 12.20 (s, 1 H), 13.86 (br, 1 H). |
| 32(*) | 80 | 1.4–1.7 (8 H, mbr), 1.8–2.0 (6 H, mbr), 4.48 (1 H, m), 6.99 (2 H, d, J = 9.2 Hz), 7.11–7.17 (3 H, m), 7.23 (1 H, t, J = 7.9 Hz), 7.67 (1 H, t, J = 8.3 Hz), 8.05 (1 H, d, J = 7.5 Hz), 8.16 (1 H, dd, J = 8.9 and 2.3 Hz), 8.58–8.63 (2 H, m), 12.23 (1 H, sbr). |

[Note]
(*) . . . $^1$H-NMR was measured in CDCl$_3$.

TABLE 9

| Compound No. | Yield (%) | $^1$H-NMR (DMSO-$d_6$):δ |
|---|---|---|
| 34 | 66 | 3.76 (2 H, s), 5.07 (2 H, s), 6.55 (1 H, dd, J = 7.7 and 1.8 Hz), 6.64 (1 H, t, J = 2.3 Hz), 6.79 (1 H, dd, J = 8.3 and 1.8 Hz), 6.98 (2 H, d, J = 8.6 Hz), 7.27 (1 H, t, J = 8.3 Hz), 7.31–7.42 (7 H, m), 7.63 (1 H, dd, J = 8.9 and 2.6 Hz), 7.88 (1 H, d, J = 2.6 Hz), 8.53 (1 H, d, J = 8.9 Hz), 11.05 (1 H, sbr), 13.91 (1 H, sbr). |
| 35(*) | 80 | 1.4–1.6 (8 H, mbr), 1.72–1.96 (6 H, m), 3.75 (2 H, s), 4.31 (1 H, quint, J = 4.0 Hz), 6.78 (2 H, d, J = 9.0 Hz), 6.92 (2 H, d, J = 9.0 Hz), 6.98 (2 H, d, J = 8.6 Hz), 7.27 (2 H, d, J = 8.6 Hz), 7.52 (1 H, dd, J = 9.2 and 2.6 Hz), 8.07 (1 H, d, |

TABLE 9-continued

| Compound No. | Yield (%) | $^1$H-NMR (DMSO-$d_6$):δ |
|---|---|---|
|  |  | J = 2.6 Hz), 8.75 (1 H, d, J = 9.2 Hz), 10.70 (1 H, sbr). |
| 37(*) | 76 | 3.81 (2 H, s), 5.05 (2 H, s), 6.64 (1 H, dd, J = 8.0 and 2.3 Hz), 6.69–6.78 (2 H, m), 6.96 (1 H, t, J = 2.3 Hz), 7.11 (2 H, d, J = 8.3 Hz), 7.23 (1 H, t, J = 8.3 Hz), 7.32 (2 H, d, J = 8.3 Hz), 7.37 (5 H, s), 7.83 (1 H, dd, J = 8.9 and 7.7 Hz), 8.59 (1 H, dd, J = 11.9 and 2.6 Hz), 11.01 (1 H, sbr). |
| 39(*) | 63 | 2.27 (3 H, s), 3.79 (2 H, s), 5.05 (2 H, s), 6.63 (1 H, dd, J = 8.3 and 2.3 Hz), 6.74 (1 H, dd, J = 8.3 and 2.3 Hz), 6.94 (1 H, t, J = 2.3 Hz), 7.09 (2 H, d, J = 8.6 Hz), 7.20 (1 H, t, J = 8.3 Hz), 7.24–7.36 (8 H, m), 7.65 (1 H, s), 8.65 (1 H, d, J = 8.6 Hz), 10.78 (1 H, sbr). |

[Note]
(*) . . . $^1$H-NMR was measured in CDCl$_3$.

TABLE 10

| Compound No. | Yield (%) | $^1$H-NMR (DMSO-$d_6$):δ |
|---|---|---|
| 41(*) | 93 | 1.4–1.6 (8 H, m), 1.74–1.92 (6 H, m), 2.27 (3 H, s), 3.74 (2 H, s), 4.29 (1 H, m), 6.77 (2 H, d, J = 9.2 Hz), 6.92 (2 H, d, J = 8.9 Hz), 6.97 (2 H, d, J = 8.6 Hz), 7.28 (2 H, d, J = 8.9 Hz), 7.38 (1 H, dd, J = 8.6 and 1.7 Hz), 7.92 (1 H, d, J = 1.7 Hz), 8.63 (1 H, d, J = 8.6 Hz), 10.67 (1 H, sbr). |
| 43(*) | 46 | 1.01 (6 H, d, J = 6.6 Hz), 2.05 (1 H, quint, J = 6.6 Hz), 3.64 (2 H, d, J = 6.6 Hz), 3.76 (2 H, s), 6.81 (2 H, d, J = 9.2 Hz), 6.93 (2 H, d, J = 9.2 Hz), 6.98 (2 H, d, J = 8.6 Hz), 7.09 (1 H, t, J = 7.5 Hz), 7.28 (2 H, t, J = 8.3 Hz), 7.59 (1 H, td, J = 7.9 Hz and 1.6 Hz), 8.11 (1 H, dd, J = 8.3 and 1.6 Hz), 8.76 (1 H, d, J = 8.3 Hz), 11.74 (1 H, sbr). |
| 45 | 68 | 3.71 (2 H, s), 5.06 (2 H, s), 6.84 (2 H, d, J = 8.58 Hz), 6.91–7.24 (10 H, m), 7.31 (2 H, d, J = 8.58 Hz), 7.56 (1 H, dd, J = 7.26, 8.25 Hz), 7.94 (1 H, dd, J = 1.32, 7.92 Hz), 8.50 (1 H, d, J = 8.25 Hz), 11.21 (1 H, s), 13.55 (1 H, br). |
| 47 | 63 | 1.37–1.80 (14 H, m), 3.77 (2 H, s), 4.48 (1 H, tt, J = 3.96, 7.92 Hz), 6.88 (2 H, d, J = 8.57 Hz), 7.02 (1 H, ddd, J = 1.65, 6.27, 8.57 Hz), 7.12–7.26 (4 H, m), 7.36 (2 H, d, J = 8.25 Hz), 7.64 (1 H, ddd, J = 1.65, 7.26, 8.57 Hz), 8.03 (1 H, dd, J = 1.65, 7.92 Hz), 8.57 (1 H, d, J = 8.57 Hz), 11.27 (1 H, s), 13.66 (1 H, br). |

[Note]
(*) . . . $^1$H-NMR was measured in CDCl$_3$

TABLE 11

| Compound No. | Yield (%) | $^1$H-NMR (DMSO-$d_6$):δ |
|---|---|---|
| 49 | 37 | 3.72 (2 H, s), 4.30 (4 H, s), 6.91 (2 H, d, J = 8.6 Hz), 6.92–7.01 (8 H, m), 7.12 (1 H, dd, J = 7.9 Hz and 7.3 Hz), 7.30 (1 H, t, J = 7.3 Hz), 7.32 (2 H, d, J = 8.6 Hz), 7.56 (1 H, ddd, J = 8.6 Hz, 7.3 Hz, and 1.7 Hz), 7.95 (1 H, dd, J = 7.9 Hz and 1.7 Hz), 8.50 (1 H, d, J = 8.6 Hz), 11.24 (1 H, brs), 13.50–13.60 (1 H, br). |
| 51 | 100 | 2.52 (1 H, ddd, J = 6.9 Hz, 6.6 Hz, and 1.3 Hz), 2.55 (1 H, ddd, J = 6.9 Hz, 6.9 Hz, and 1.3 Hz), 3.72 (2 H, s), 3.87 (3 H, s), 3.99 (2 H, t, J = 6.9 Hz), 5.11 (1 H, dd, J = 10.2 Hz, and 1.7 Hz), 5.17 (1 H, dd, J = 17.1 Hz, and 1.7 Hz), 5.86–5.90 (1 H, m), 6.90 (2 H, d, J = 8.6 Hz), 6.96 (4 H, s), 7.13 (1 H, dd, J = 7.6 Hz, and 7.3 Hz), 7.32 (2 H, d, J = 8.6 Hz), 7.57 (1 H, dd, J = 8.6 Hz, and 7.6 Hz), 7.95 (1 H, d, J = 7.3 Hz), 8.50 (1 H, d, J = 8.6 Hz), 11.13 (1 H, brs), 13.50–13.60 (1 H, br). |
| 53 | 80 | 0.90 (6 H, t, J = 7.3 Hz), 1.33–1.50 (4 H, m), 1.57–1.66 (1 H, m), 3.72 (2 H, s), 3.82 (2 H, d, J = 5.9 Hz), 6.90 (2 H, d, J = 8.6 Hz), 6.96 (4 H, s), 7.13 (1 H, dd, J = 7.6 Hz, and 7.3 Hz), 7.32 (2 H, d, J = 8.6 Hz), 7.57 (1 H, dd, J = 8.6 Hz, and 7.6 Hz), 7.95 (1 H, d, J = 7.3 Hz), 8.50 (1 H, d, J = 8.6 Hz), 11.13 (1 H, brs), 13.50–13.60 (1 H, br). |
| 55 | 100 | 0.98 (3 H, t, J = 7.3 Hz), 1.45–1.64 (2 H, m), 1.71–1.82 (2 H, m), 3.72 (2 H, s), 3.93 (2 H, t, J = 6.6 Hz), 6.90 (2 H, d, J = 8.6 Hz), 6.96 (4 H, s), 7.13 (1 H, dd, J = 7.6 Hz, and 7.3 Hz), 7.32 (2 H, d, J = 8.6 Hz), 7.57 (1 H, dd, J = 8.6 Hz, and 7.6 Hz), 7.95 (1 H, d, J = 7.3 Hz), 8.50 (1 H, d, J = 8.6 Hz), 11.13 (1 H, brs), 13.50–13.60 (1 H, br). |

Example 10
Measurement of human IgE antibody production-inhibiting activity in vitro In accordance with the following method established with reference to The Journal of Immunology (J. Immunol.), Vol. 146, 1836 to 1842 (1991) and the Journal of Immunology (J. Immunol.), Vol. 147, 8 to 13 (1991), the concentrations of IgE and IgE antibodies, when the compounds of the present invention shown in Table 12 were employed, were measured.

Peripheral venous blood gathered from a healthy person was subjected to a density-gradient centrifugation to isolate lymphocytes therefrom. The isolated lymphocytes were washed and suspended in a culture medium liquid (RPMI-1640 (made by Gibco Co.)+10% heat-inactivated FCS (made of Whittaker Co.)+100 μg/ml streptomycin+100 U/ml penicillin G+2 mM L-glutamine). As the compounds to be tested, the compounds shown in Table 2 were employed. The lymphocytes in the suspension were cultured for one week in the presence or non-presence of the above-mentioned compounds and in the presence of an interleukin 4 (IL-4, made by GENZYME CO.) (0.1 mg/ml), an anti-CD 40 antibodies (anti CD 40 Ab, made by BIOSOURCE CO., clone B-B20) (0.2 mg/ml), and an interleukin 10 (IL-10, made by GENZYME CO.) (0.2 mg/ml). To this culture system, the same culture medium liquid as mentioned above was supplemented, and then the culture was further carried out for one week. Thereafter, the concentrations of IgE antibodies and IgG antibodies in the supernatant of the culture mixture were measured by a sandwich ELISA method. In the measurement by the ELISA method, the concentration of the IgE antibodies was determined by using a primary antibody consisting of a rabbit anti-human IgE (ε) antibody (made by IGN Co.) and a secondary antibody consisting of biotin-anti-human IgE monoclonal antibody (G7-26, made by Phar Mingen Co.), and the concentration of IgG antibodies was determined by using a primary antibody consisting of anti-human IgG monoclonal antibody (G18-145, made by Phar Mingen Co.) and a secondary antibody consisting of biotin-donkey anti-human IgG antibody (H+L), made by Jackson Co.). Also, in the measurement of IgE and IgG antibody concentrations, as an enzyme, an Avidin-Biotin-HRP (Avidin-Biotin-Horse Radish Peroxidase; ABC kit, made by Vector Lab.) was used and as a substrate, TMB (3,3′, 5,5′-tetramethylbenzidine) Microwell Peroxidase Substrate System (made by Kirkegaad & Perry Laboratories Inc.) was used.

On the basis of each antibody concentration when the compound of the present invention was not present, each antibody production-inhibition (%) in a concentration of the compound to be tested of 0.1 μM was calculated. Further, with respect to some of the compounds tested, the antibody production-inhibitions (%) of the tested compounds were measured in various concentrations thereof, and IC 50 values thereof were calculated. (Refer to Uejima et al., American Academy of Allergy & Immunology, Proceeding of 1995 Annual Meeting, Program No. 818). The measurement results are shown in Table 12.

TABLE 12

Antibody production-inhibiting performance of the compounds of the present invention (100 nM)

| Compound No. | IgE antibody production-inhibition (%) | IgG antibody production-inhibition (%) | $IC_{50}$ (nM) (IgE) | $IC_{50}$ (nM) (IgG) |
|---|---|---|---|---|
| 4 | 100 | 100 | 28 | 200 |
| 8 | 95.5 | 40.6 | 17 | 50 |
| 12 | 100 | 95.8 | 44 | >100 |
| 14 | 100 | 93.8 | 6 | 12 |
| 16 | 100 | 95.8 | 22 | 46 |
| 18 | 19.5 | −1.7 | NT | NT |
| 20 | 100 | 52.6 | 35 | >100 |
| 22 | 51.0 | −33.2 | NT | NT |
| 30 | 25.7 | −31.7 | NT | NT |

Note:
NT . . . No measurement was carried out.

From the results shown in Table 2, it was confirmed that the compounds of the present invention exhibited antibody production-inhibiting performance, and the inhibiting performance is stronger with respect to IgE.

Accordingly, the compounds of the present invention were confirmed to be useful as prophylactic and/or therapeutic medicine for allergic diseases derived from the IgE antibody production, for example, bronchial asthma, allergic rhinitis, allergic conjunctivitis, atopic dermatitis, anaphylactic shock, mite allergy, pollinosis, food allergy,.urticaria, ulcerative gastroenteritis, eosinophilic gastroenteritis and medicamentosus exanthema.

Example 11
Measurement of IgE antibody production-inhibiting performance on TNP-sensitive mice TNP-KLH (2 μg/head) and Alum (1 mg/head) were dosed into the abdominal cavities of 8-week-old male mice to sensitize the mice.

Compound No. 14 was suspended in a concentration of 1.0 mg/ml, 3.0 mg/ml or 1.0 mg/me in an aqueous 5% gum arabi solution, and each suspension was perorally dosed to three groups of mice for medication, to which each medicine was dosed at a dosage of 10 ml/kg, (namely, 10 mg/kg, 30 mg/kg or 100 mg/kg), once a day continuously for 10 days from the sensitized day. For a vehicle mouse group, the above-mentioned aqueous gum arali solution was dosed in the same amount as mentioned above in the same manner as mentioned above.

On the day after the final dosing day (the eleventh day), blood was extracted from the heart of the mouse, and a TNP specific antibody value of a blood serum obtained from the extracted blood was measured in accordance with ELISA method. The measurement results are shown in Table 13.

TABLE 13

|  | anti-TNP IgE (ng/ml) | anti-TNP IgG (ng/ml) | anti-TNP IgM (μg/ml) |
|---|---|---|---|
| Vehicle group | 433 ± 118 | 4390 ± 2630 | 110 ± 9 |
| 10 mg/kg dosed group | 127 ± 72 | 2980 ± 2310 | 79 ± 40 |
| 30 mg/kg dosed group | 52 ± 30** | 2500 ± 1700 | 73 ± +26 |
| 100 mg/kg dosed group | 0.2 ± 0.4** | 16 ± 18** | 20 ± 5.0** |

** p < 0.01 vs. vehicle

As shown in Table 13, a class-selective anti TNP IgE antibody production-inhibiting performance due to the dosage of the compounds of the present invention was recognized in the 30 mg/kg dosed group. In the 100 mg/kg dosed group, a class-non-selective TNP antigen-specific antibody production-inhibiting performance was recognized. In the animals used for this experiment, in comparison with the vehicle group of animals after the dosage, an increase in weight-inhibiting performance and an increase in spleen weight-inhibiting performance were not recognized. Namely, it was recognized that due to the dosage of the compounds of the present invention, the production of allergen-specific antibodies in the blood serum was IgE class-selectively inhibited.

Example 12

Production of tablets

Tablets having the following composition were produced.

| Component | Weight content per tablet |
|---|---|
| Compound No. 4 | 250 mg |
| Lactose | 230 mg |
| Potato starch | 80 mg |
| Polyvinylpyrrolidone | 11 mg |
| Magnesium stearate | 5 mg |

In the production, Compound No. 4 was mixed with lactose and potato starch, the resultant mixture was uniformly wetted with a 20% polyvinylpyrrolidone solution in ethyl alcohol, the wetted mixture was passed through a 20 nm mesh-size sieve, and dried at a temperature of 45° C., and the dried mixture was passed through a 15 nm mesh size sieve. The resultant granules were mixed with magnesium stearate and the mixture was molded under compression to provide tablets.

We claim:

1. Benzene derivatives of the formula (I):

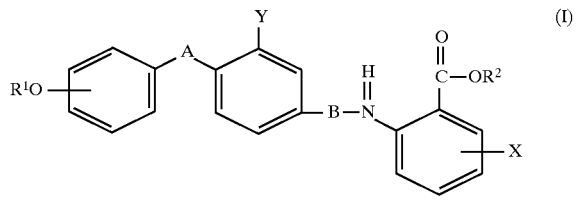

in which formula (I), $R^1$ represents a hydrogen atom, a $C_1$ to $C_{12}$ cyclic, straight chain or branched chain alkyl group which may be substituted with at least one $C_6$ to $C_{10}$ aryloxy group, a $C_7$ to $C_{12}$ aralkyl group of which the aryl group may be substituted by at least one member selected from halogen atoms, a methyl group and a methoxy group, or a $C_3$ to $C_{10}$ alkenyl group which may be substituted by at least one phenyl group; A represents an —O—, —S— or —CH$_2$— group; B represents an —O—, or —CZ$_2$CO— group in which Z represents a hydrogen atom or a fluorine atom; $R^2$ represents a hydrogen atom, or a $C_1$–$C_4$ lower alkyl group; X represents a hydrogen atom, a halogen atom or a methyl group; and Y represents a hydrogen atom, a nitro group or a nitrile group, or pharmacologically acceptable salts thereof or pharmacologically acceptable solvates of the above-mentioned benzene derivatives and salts thereof.

2. The benzene derivatives, pharmacologically acceptable salts thereof, pharmacologically acceptable solvates of the above-mentioned benzene derivatives and salts thereof as claimed in claim 1, wherein in the formula (I), $R^1$ represents a hydrogen atom, a $C_1$ to $C_{12}$ alkyl group or a $C_7$ to $C_{12}$ aralkyl group; A represents an —O— bond; and B represents a —CO— group or a —CH$_2$CO— group.

3. The benzene derivatives, pharmacologically acceptable salts thereof, or pharmacologically acceptable solvates of the above-mentioned benzene derivatives and salts thereof as claimed in claim 2, wherein in the formula (I), $R^1$ represents a hydrogen atom, a $C_5$ to $C_{12}$ cyclic alkyl group, a $C_3$ to $C_8$ branched chain alkyl group or a benzyl group; A represents an —O— bond; R represents a —CH$_2$CO— group; and $R^2$ represents a hydrogen atom.

4. The benzene derivatives, pharmacologically acceptable salts thereof, or pharmacologically acceptable solvates of the above-mentioned benzene derivatives and salts thereof as claimed in claim 2, wherein in the formula (I); $R^1$ represents a $C_5$ to $C_{12}$ cyclic alkyl group, a group represented by the general formula;

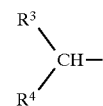

wherein $R^3$ and $R_4$ respectively and independently from each other represent a methyl, ethyl or n-propyl group, or a benzyl group.

5. The benzene derivatives, pharmacologically acceptable salts thereof, or pharmacologically acceptable solvates of the above-mentioned benzene derivatives and salts thereof as claimed in claim 1, wherein in the formula (I), B represents a —CH$_2$CO— group.

6. The benzene derivatives, pharmacologically acceptable salts thereof or pharmacologically acceptable solvates of the above-mentioned benzene derivatives and salts thereof as claimed in claim 1, wherein in the formula (I), $R^2$ represents a hydrogen atom or a methyl group.

7. The benzene derivatives, pharmacologically acceptable salts thereof, or pharmacologically acceptable solvates of the above-mentioned benzene derivatives and salts thereof as claimed in claim 1, wherein in the formula (I), the substituent represented by X is located in a 4- or 5-position of the benzene ring to which the substituent is attached with respect to the —COOR$^2$ group.

8. The benzene derivatives, pharmacologically acceptable salts thereof, or pharmacologically acceptable solvates of the above-mentioned benzene derivatives and salts thereof as claimed in claim 1, wherein in the formula (I), the substituent represented by R$^1$O is located in a 4-position of the benzene ring to which the substituent is attached, with respect to the A group.

9. Pharmaceutical compositions comprising the benzene derivatives, pharmacologically acceptable salts thereof, or pharmacologically acceptable solvates of the above-mentioned benzene derivatives and salts thereof as claimed in claim 1 and pharmaceutically acceptable carriers.

10. Prophylactic or therapeutic medicines for allergic diseases, characterized by comprising, as an active ingredient, the pharmaceutical composition as claimed in claim 9, and having inhibitory effects on the production of IgE antibodies.

11. The prophylactic or therapeutic medicines for allergic diseases as claimed in claim 10, wherein the allergic diseases include bronchial asthma, allergic rhinitis, allergic conjunctivitis, atopic dermatitis, anaphylactic shocks, mite allergy, pollinosis, and food allergy.

12. The benzene derivative, pharmacologically acceptable salts thereof, or pharmacologically acceptable solvates of the above-mentioned benzene derivatives and salts thereof as claimed in claim 2, wherein in the formula (I), B represents a —CH$_2$CO— group.

13. The benzene derivatives, pharmacologically acceptable salts thereof, or pharmacologically acceptable solvates of the above-mentioned benzene derivatives and salts thereof as claimed in claim 2, wherein in the formula (I), the substituent represented by R$^1$O is located in a 4-position of the benzene ring to which the substituent is attached, with respect to the A group.

14. The benzene derivatives, pharmacologically acceptable salts thereof, or pharmacologically acceptable solvates of the above-mentioned benzene derivatives and salts thereof as claimed in claim 3, wherein in the formula (I), the substituent represented by R$^1$O is located in a 4-position of the benzene ring to which the substituent is attached, with respect to the A group.

15. The benzene derivatives, pharmacologically acceptable salts thereof, or pharmacologically acceptable solvates of the above-mentioned benzene derivatives and salts thereof as claimed in claim 4, wherein in the formula (I), the substituent represented by R$^1$O is located in a 4-position of the benzene ring to which the substituent is attached, with respect to the A group.

* * * * *

UNITED STATES PATENT AND TRADEMARK OFFICE
CERTIFICATE OF CORRECTION

PATENT NO. : 5,808,144  
DATED : September 15, 1998  
INVENTOR(S) : Masaichi Hasegawa et al.

Page 1 of 1

It is certified that error appears in the above-identified patent and that said Letters Patent is hereby corrected as shown below:

<u>Title page,</u>
Item [56], should read as follows:

-- [56]   References Cited

FOREIGN PATENT DOCUMENTS 1 276 359   6/1972   (GB)

PUBLICATIONS

Database CAPLUS, No. 120:134055, Oe et al., "Preparation of arylalkananilides as ACAT inhibitors (WO9315043)," abstract, Aug. 5, 1993. --

<u>Column 26,</u>
Line 20, after "B represents an" replace "- O -" with -- CO --.

Signed and Sealed this

Eighteenth Day of November, 2003

JAMES E. ROGAN
*Director of the United States Patent and Trademark Office*